United States Patent [19]

Eisenberg

[11] Patent Number: 4,653,490

[45] Date of Patent: Mar. 31, 1987

[54] THUMB RESTRAINT

[76] Inventor: Joel H. Eisenberg, 53A Blackhawk La., Stratford, Conn. 06497

[21] Appl. No.: 763,346

[22] Filed: Aug. 7, 1985

Related U.S. Application Data

[63] Continuation of Ser. No. 604,506, Apr. 27, 1984, Pat. No. 4,565,195, which is a continuation of Ser. No. 219,481, Dec. 23, 1982, Pat. No. 4,445,507.

[51] Int. Cl.[4] .............................................. A61F 13/00
[52] U.S. Cl. .................................... 128/133; 128/87 A
[58] Field of Search ................... 128/133, 165, 87 A; 2/16, 18–19, 161 A, 161 R, 159

[56] References Cited

U.S. PATENT DOCUMENTS

| 381,687 | 4/1888 | Fischer | 2/19 |
|---|---|---|---|
| 1,471,948 | 10/1923 | Cox et al. | 128/87 A |
| 1,509,801 | 9/1924 | Walters | 2/19 |
| 1,627,382 | 5/1927 | Golomb | 2/18 |
| 1,817,212 | 8/1931 | Siebrandt | 128/87 A |
| 1,837,691 | 12/1931 | Thigpen | 128/87 A |
| 1,951,190 | 3/1934 | Gambee | 2/21 |
| 2,388,330 | 11/1945 | Jungmann | 2/161 |
| 2,498,122 | 2/1950 | Haniuk | 128/133 |
| 2,523,606 | 9/1950 | Young | 128/87 A |
| 2,633,126 | 3/1953 | Newmark | 128/133 |
| 3,182,657 | 5/1965 | Zurbuchen | 128/133 |
| 3,189,073 | 6/1965 | Todd | 128/133 |
| 3,416,158 | 12/1968 | Kulman | 2/161 |
| 3,724,456 | 4/1973 | Waxman | 128/133 |
| 3,882,548 | 5/1975 | Shienagawa et al. | 2/161 |
| 4,137,572 | 2/1979 | Jansson et al. | 2/16 |
| 4,173,218 | 11/1979 | Cronin | 128/77 |
| 4,243,026 | 1/1981 | Barber | 128/77 |
| 4,287,610 | 9/1981 | Rhee | 2/18 |
| 4,295,229 | 10/1981 | Clark et al. | 2/20 |
| 4,438,532 | 3/1984 | Campanella et al. | 2/16 |

Primary Examiner—C. Fred Rosenbaum
Assistant Examiner—C. W. Shedd

[57] ABSTRACT

A glove having a retainer disposed adjacent to the outside of a thumb portion so as to restrict movement of the thumb portion away from the rest of the glove thereby preventing damage to certain ligaments of the user's thumb should the thumb be bent abnormally.

4 Claims, 6 Drawing Figures

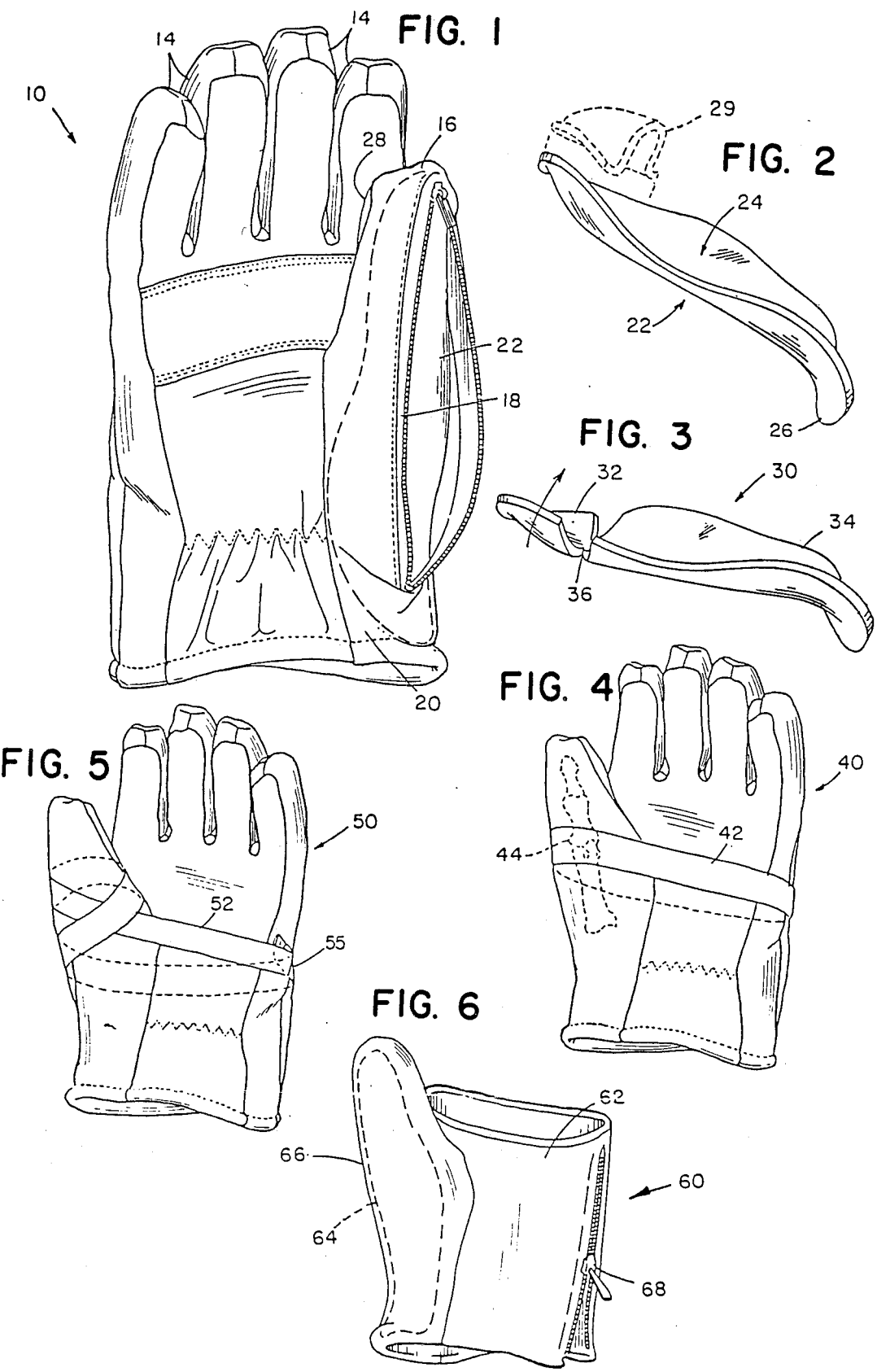

THUMB RESTRAINT

This application is a continuation of application Ser. No. 604,506, filed Apr. 27, 1984, now U.S. Pat. No. 4,565,195, which is a continuation of application Ser. No. 219,481 filed Dec. 23, 1982, now U.S. Pat. No. 4,445,507.

FIELD OF THE INVENTION

This invention relates to the field of protective handwear, particularly in regard to preventing damage to certain ligaments of the thumb.

BACKGROUND OF THE INVENTION

In various sports and recreational activities, as well as in industry, there are numerous occasions when, as a result of a fall or other event, the thumb is momentarily bent away from the other fingers of the hand. This bending results in a stretching of the ulnar collateral ligament, which is connected around the thumb's lower joint, the metacarpal phalangeal joint. If this stretching is severe enough, the ligament will rupture, and as it will frequently not heal by itself, surgery is often required to repair the tear. Even if the ligament is not torn, such a stretching, particularly if repeated, will loosen the ligament giving rise to a chronic wobbling of the joint, which could cause arthritis.

Prior art gloves and handwear are, at best, only designed to protect the hand from cold or from abrasions and do not prevent such ligament damage at all. Furthermore, the common way to protect the thumb area after surgery is by using a cumbersome cast, which cannot, as a practical matter, be kept on the hand for longer than six to eight weeks, a time period far short of that actually required for the ligament to mature.

SUMMARY OF THE INVENTION

I have discovered that stress on the ulnar collateral ligament can be greatly reduced while allowing the thumb and hand normal freedom of movement by positioning a restraint in a glove so that the restraint limits abnormal movement of the thumb when the glove is on the hand.

In a preferred embodiment, an inflexible retaining trough is disposed inside a pocket along the radial side (outside) of the thumb of the glove. The trough extends from the tip of the thumb down to the wrist area. When the hand is in place in the glove, the outside of the thumb, the carpal bones and the distal radius are cradled by the trough thereby preventing any movement of the thumb away from the fingers or any other abnormal thumb movement. However, the ulnar (inside) portion of the glove's thumb has enough loose fabric so that the thumb can bend normally, i.e., towards the palm of the hand. The glove of this embodiment may be relatively heavy and therefore particularly suited for use in skiing or in hockey.

In another preferred embodiment of the invention, the glove has a retaining ribbon extending around its outside so that when a hand is placed in the glove, the ribbon extends from the metacarpal phalangeal joint area of the thumb to the lower portion of the ulnar (little finger) side of the hand thereby restricting outward movement of the thumb while not inhibiting its normal flexing. Gloves of this embodiment may be lightweight and therefore particularly suitable for karate, weight-lifting or a general purpose work glove.

The gloves of these embodiments may also be used as post-surgical protection for a repaired ulnar collateral ligament after the cast has been removed. To reduce glove weight for this purpose, the gloves of these embodiments can also be made without fingers and with a truncated thumb and with a slit side to allow the glove to be put on easily.

DESCRIPTION OF THE PREFERRED EMBODIMENT

I turn now to the description of the preferred embodiment after first describing the drawings.

Drawings

FIG. 1 is a perspective view of a glove of this invention;

FIG. 2 is a perspective view of a retainer of this invention;

FIG. 3 is a perspective view of another retainer of this invention;

FIG. 4 is a perspective view of another glove of this invention;

FIG. 5 is a perspective view of another glove of this invention; and

FIG. 6 is a perspective view of another glove of this invention.

STRUCTURE

Referring to FIG. 1, a glove according to the invention herein is shown at 10. The glove 10 has an outer shell 12 having four fingers 14 and a thumb pocket 16. A zippered pocket 18 (shown open) is disposed on the ulnar side (outside) of the thumb pocket 16. Pocket 18 extends from the top of the thumb pocket 16 to near a wrist 20 of the glove 10.

A retaining trough 22, shown in FIG. 2, fits into the pocket 18 and extends the length thereof. Trough 22 is curved having a hollow section 24 extending its entire length. The hollow section 24 conforms to the radial side of a thumb and hand down to the wrist area. A lip 26 is disposed on the wrist end of the trough 22. The trough 22 may be made of fiberglass, or any other material which can easily be molded but is lighweight and inflexible when hardened.

As for normal movement of the thumb, the loose fabric 28 on the ulnar side of the thumb pocket 16 permits the thumb to flex at its top joint, the interphalangeal joint. Proper flexion at the lower joint is also not seriously inhibited. Thus, the normal movement of the thumb is not affected by the retaining trough 22. It should be understood that the term loose fabric in this context does not mean an abundance of fabric, as the fabric of the inside of a thumb pocket of a conventional ski glove would be loose enough for this purpose.

The zippered pocket 18 of the glove 10 of the preferred embodiment is only used to provide a means for removal of the trough 22, if desired. The trough 22 could also be placed inside a closed, unzippered pocket, which is then sewn onto the structure of an existing glove. Also, the trough could be directly attached to the outside of a thumb pocket of a glove without a surrounding pocket. For comfort, the trough 22 itself may be padded or molded to the exact shape of the thumb and radial side of the user's hand.

When a hand is in place inside the glove 10, the radial side of the hand and its thumb fits into the trough 22. The trough 22 essentially holds the radial side of the first ray (the thumb and the metacarpal) of the hand. A layer of fabric (not shown) forming the inside of the zippered pocket 18 is disposed between the thumb and the trough 22. If desired, this layer may be omitted.

For additional protection, a semi-cylindrical thumb piece 29 (shown dotted in FIG. 2) may be added to cover the ulnar side of the thumb, which is then completely surrounded by the trough 22 and thumb piece 29. The thumb piece 29 may be flexible to allow the thumb to bend normally.

Operation

If any pressure is applied to the ulnar side (inside of the thumb pocket 16, the thumb inside the pocket 16 is forced back against the hollow section 24 of the trough 22 and the radial carpal bones and distal radius fit into the trough 22. Further radial movement of the thumb by itself is essentially impossible as the trough 27 has essentially frozen the bones forming the lower thumb joint in the radial direction. Little abnormal (i.e., other than the natural flexion of the joint) movement of one bone with respect to the other is possible. The ulnar collateral ligament is not significantly stretched, and no damage to it results. The curved lip 26 at the lower end of the trough prevents the trough from digging into the wrist of the wearer.

Other Embodiments

As shown in FIG. 3, a retaining trough 30 may be comprised of a thumb piece 32 and a lower piece 34, connected by a hinge 36. The hinge 36 only bends forwardly and does not allow rearward movement. When the hand is in place, the hinge 36 is located adjacent to the upper joint of the thumb. This two-piece arrangement with the hinge 36 permits normal movement of the thumb without the need for loose fabric on the ulnar side of a thumb pocket. The same hinge effect can be achieved by using a single piece trough made of a material which flexes only in the direction of normal thumb movement and is inflexible in other directions. The hinge and thumb piece structure may also be formed by using a series of overlapping sections arranged so that the lower part of a first section, which section extends from the tip of the thumb beyond its first joint, overlaps the top portion of a second section extending between the first and second joint. This permits the thumb to bend normally but restricts abnormal movement.

Another embodiment of this invention is shown in FIG. 4. A ribbon 42 extends circumferentially around the outside of a glove 40. When a hand is inside the glove 40, the ribbon 42 is effectively wrapped over and above the metacarpal phalangeal joint 44 of the thumb on one side of the hand and the ulnar side (little finger side) of the hand. The ribbon 42 restricts the outward movement of the thumb and thereby protects the ulnar collateral ligament. The ribbon also may be positioned around the inside of the glove, and in fact it need not go completely around the glove at all.

Another embodiment of this invention is shown in FIG. 5. A glove 50 has a ribbon 52 which is wrapped around the thumb area so that it covers the metacarpal phalangeal joint and then extends to the other (ulnar) side of the hand near the wrist area. The tightness of the ribbon 52 (and also the ribbon 42 of the embodiment of FIG. 4) may be adjusted by pulling the ends of the ribbon in the ulnar direction. The ends of the ribbon, which overlap on the ulnar side of the hand, have adjacent Velco surfaces so as to form an adjustable fastener 55. Other such fastening means, i.e., drawstrings, may also be used. The ribbons 42, 52 may be partially or entirely elastic so that the thumb is closely held to the hand but can be actively brought away from the hand by muscle power and assisted to return to the hand by the ribbon's elasticity.

Another embodiment is shown in FIG. 6. A glove 60 is comprised of a cloth 62 which wraps around a hand. A retainer 64, like that of FIG. 2, is attached to the cloth 62 inside a pocket 66 so that when the cloth 62 is in place, the outside of the thumb and hand fits in the retainer 64. The cloth is held in place by fastening zipper 68 which is on the ulnar side of the hand when the cloth 62 is in place. To make the glove adjustable the zipper may be omitted and velcreau fastener used instead. This embodiment is particularly useful in post-surgical applications where it may be undesirable to force the repaired hand through the narrow wrist opening of a conventional glove.

It is also possible to use the embodiment of FIG. 6, of a similar truncated glove, having the ribbons of FIGS. 4, 5, as an insert for a conventional glove.

In each case, the invention limits the abnormal movement through which the metacarpal phalangeal joint of the thumb may be brought. It further restricts the speed at which any extension occurs so that the elastic limit of the ligaments is not exceeded which would cause a rupture.

Other embodiments will occur to those skilled in the art.

What is claimed is:
1. A glove for preventing injury to the thumb's ulnar collateral ligament comprising:
    a hand covering comprising a cloth, said cloth being wrapped around the hand when said glove is in place,
        said hand covering having a thumb portion said thumb portion having a retainer means disposed at least in part on the radial side of said thumb portion,
        said retainer means being inflexible in the radial direction, and when the wearer's thumb is in place in said thumb portion of said glove, said retainer means is disposed to extend over the thumb's metacarpal phalangeal joint and is of sufficient length to also extend over substantial portions of the adjacent bones which form the joint so as to generally immobilize the bones with respect to the joint in the radial direction whereby radial movement of the thumb which might injure the ulnar collateral ligament of the thumb is prevented.
2. The glove of claim 1 wherein said cloth is fastened by a zipper, said zipper joining the ends of said cloth along the ulnar side of the hand.
3. The glove of claim 1 wherein said retainer means comprises an inflexible trough disposed in a pocket in said cloth so that said trough is disposed along the radial side of a thumb when said glove is on a hand.
4. The glove of claim 1 wherein said retaining means comprises a series of overlapping sections, said sections allowing the thumb to bend normally but restricting abnormal bending when said glove is in place.

* * * * *